(12) United States Patent
Cahoon et al.

(10) Patent No.: US 7,834,247 B2
(45) Date of Patent: Nov. 16, 2010

(54) PLANT FARNESYLTRANSFERASES

(75) Inventors: Rebecca E. Cahoon, Lincoln, NE (US); Timothy George Helentjaris, Tucson, AZ (US); Guo-Hua Miao, Shanghai (CN)

(73) Assignees: E.I. du Pont de Nemours and Company, Wilmington, DE (US); Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 12/732,309

(22) Filed: Mar. 26, 2010

(65) Prior Publication Data

US 2010/0184605 A1  Jul. 22, 2010

Related U.S. Application Data

(60) Division of application No. 12/536,203, filed on Aug. 5, 2009, now Pat. No. 7,737,330, which is a division of application No. 11/955,511, filed on Dec. 13, 2007, now Pat. No. 7,589,258, which is a division of application No. 11/505,151, filed on Aug. 16, 2006, now Pat. No. 7,348,469, which is a division of application No. 10/773,529, filed on Feb. 6, 2004, now Pat. No. 7,109,391, which is a continuation of application No. 09/786,675, filed as application No. PCT/US99/20419 on Sep. 7, 1999, now abandoned.

(60) Provisional application No. 60/099,521, filed on Sep. 8, 1998.

(51) Int. Cl.
*A01H 5/00* (2006.01)
*C12N 15/82* (2006.01)
*C12N 5/14* (2006.01)
*C12N 15/63* (2006.01)
*C12N 15/81* (2006.01)
*C07H 21/04* (2006.01)

(52) U.S. Cl. .................... 800/295; 800/278; 800/279; 435/69.1; 435/320.1; 435/468; 536/23.1

(58) Field of Classification Search ....................... None
See application file for complete search history.

(56) References Cited

U.S. PATENT DOCUMENTS

| 2001/0044938 | A1 | 11/2001 | McCourt et al. |
| 2003/0061636 | A1 | 3/2003 | McCourt et al. |
| 2003/0167535 | A1 | 9/2003 | Huang et al. |
| 2004/0001821 | A1 | 1/2004 | Silver et al. |

FOREIGN PATENT DOCUMENTS

WO          9906580          2/1999

OTHER PUBLICATIONS

Qian et al. (Plant Cell 8:2381-2394; 1996).*

Daqi Quian et al., Plant Cell vol. 8, p. 2381-2394, 1996, Protein Farnesyltransferase in Plants: Molecular Characterization and Involvement in Cell Cycle Control.
Zhenbiao Yang et al., Plant Phys., vol. 101(2), p. 667-674, 1993, Protein Farnesyltransferase in Plants.
Sean Cutler et al., Science, vol. 273, p. 1239-1241, 1996, A Protein Farnesyl Transferase Involved in Abscisic Acid Signal Transduction in Arabidopsis.
S. Yalovsky et al., Mol. & Cell. Biol., vol. 17(4), p. 1986-1994, 1997, Plant Farnesyltransferase Can Restore Yeast RAS Signaling and Mating.
Shingo Hata et al., Plant Cell Physiol., vol. 38(12), p. 1409-1413, 1997, CDNA Cloning of Squalene Synthase Genes From Mono- and Dicotyledonous Plants, and Expression of the Gene in Rice.
Sylvain Merlot et al., Plant Physiol., vol. 114, p. 751-757, 1997, Genetic Analysis of Abscisic Acid Signal Transduction.
E. Skoczylas et al., Biochimie, vol. 78, p. 139-143, 1996, Protein Farnesyltransferase in Plants.
Christopher C. Farnsworth et al., PNAS, vol. 91, p. 11963-11967, 1994, RAB Geranylgeranyl Transferase Catalyzes in Geranylgeranylation of Adjacent Cysteines in the Small GTPases RAB1A, RAB3A, and RAB5A.
Zhen-Ming Pei et al., Science, vol. 282, p. 287-290, 1998, Role of Farnesyltransferase in ABA Regulation of Guard Cell Anion Channels and Plant Water Loss.
National Center for Biotechnology Information General Identifier No. 2246442, Accession No. AAB62580, 1997, Qian, D. et al., Protein Farnesyltransferase in Plants: Molecular Characterization and Involvement in Cell Cycle Control.
National Center for Biotechnology Information General Identifier No. 3142698, Accession No. AAC61853, 1998, Belbahrl et al.
National Center for Biotechnology Information General Identifier No. 1184953, Accession No. AAA87585, 1996, Cutler, S.R., et al.
National Center for Biotechnology Information General Identifier No. 266753, Accession No. Q02293, 2003, Chen, W.J., et al., CDNA Cloning and Expression of the Peptide-Binding BETA Subunit of Rat P21RAS Farnesyltransferase, the Counterpart of Yeast DPR1/RAM1.
National Center for Biotechnology Information General Identifier No. 8347240, 2000, Accession No. AAF74564, Ziegelhoffer, E.C., et al., Cloning of the *Arabidopsis* Wiggum Gene Indentifies a Role for Farnesylation in Meristem Development.
Eva C. Ziegelhoffer et al., PNAS, vol. 97(13), p. 7633-7638, 2000, Cloning of the *Arabidopsis* Wiggum Gene Identifies a Role for Farnesylation in Meristem Development.
Hee-Won Park et al., Science, vol. 275, p. 1800-1804, 1997, Crystal Structure of Protein Farnesyltransferase at 2.25 Angstrom Resolution.
Shaul Yalovsky et al., The Plant Cell, vol. 12 p. 1267-1278, 2000, Functional Requirement of Plant Farnesyltransferase During Development in *Arabidopsis*.

(Continued)

*Primary Examiner*—Vinod Kumar

(57) ABSTRACT

This invention relates to an isolated nucleic acid fragment encoding a farnesyltransferase subunit. The invention also relates to the construction of a chimeric gene encoding all or a portion of the farnesyltransferase subunit, in sense or antisense orientation, wherein expression of the chimeric gene results in production of altered levels of the farnesyltransferase subunit in a transformed host cell.

11 Claims, No Drawings

OTHER PUBLICATIONS

National Center for Biotechnology Information General Identifier No. 1815668, Accession No. AAC49666, 19997, Yalovsky, S. et al., Plant Farnesyltransferase Can Restore Yeast RAS Signaling and Mating.

National Center for Biotechnology Information General Identifier No. 417482, Accession No. Q04903, 2000, Yang, Z. et al., Protein Farnesyltransfer in Plants, Molecular Cloning and Expression of a Homolog of the Beta Subunit From the Garden Pea.

National Center for Biotechnology Information General Identifier No. 169049, Accession No. AAA33649, 1993, Yang Z. et al., Protein Farnesyltransfer in Plants, Molecular Cloning and Expression of a Homolog of the Beta Subunit From the Garden Pea.

Lassaad Belbahri et al., Plant Phys., vol. 118, p. 329-331, 1998, Nucleotide Sequence of a Putative Protein Farnesyltransferase Subunit a From *Arabidopsis*.

Arnaud Galichet et al., Current Opinion in Plant Biology, vol. 6, p. 530-535, 2003, Protein Farnesylation in Plants—Conserved Mechanisms but Different Targets.

Douglas, A. Andrest et al., The Journal of Biological Chemistry, vol. 268, p. 1383-1390, 1993, Mutational Analysis of Alpha-Subunit of Protein Farnesyltransferase.

* cited by examiner

PLANT FARNESYLTRANSFERASES

This application is a divisional of U.S. application Ser. No. 12/536,203, filed Aug. 5, 2009, now U.S. Pat. No. 7,737,330, issued Jun. 15, 2010, which is a divisional of U.S. application Ser. No. 11/955,511, filed Dec. 13, 2007, now U.S. Pat. No. 7,589,258, issued Sep. 15, 2009, which is a divisional of U.S. application Ser. No. 11/505,151, filed Aug. 16, 2006, now U.S. Pat. No. 7,348,469, issued Mar. 25, 2008, which is a divisional of U.S. application Ser. No. 10/773,529, filed Feb. 6, 2004, now U.S. Pat. No. 7,109,391, issued Sep. 19, 2006, which is a continuation of U.S. application Ser. No. 09/786,675, filed Mar. 7, 2001, now abandoned, which is a 35 U.S.C. 371 National Stage Application of International Application No. PCT/US99/20419, filed Sep. 7, 1999, now expired, which claims the benefit of U.S. Provisional Application No. 60/099,521, filed Sep. 8, 1998, now expired.

FIELD OF THE INVENTION

This invention is in the field of plant molecular biology. More specifically, this invention pertains to nucleic acid fragments encoding farnesyltransferase subunits in plants and seeds.

BACKGROUND OF THE INVENTION

Lipids and proteins associate covalently to form lipid-linked proteins and noncovalently to form lipoproteins. The lipid portions of lipid-linked proteins anchor their attached proteins to membranes and mediate protein-protein interactions. Proteins form covalent attachments to lipids in several ways, one of which is the covalent attachment of isoprenoid groups, mainly the $C_{15}$ farnesyl and $C_{20}$ geranylgeranyl residues.

In mammals, geranylgeranyltransferase is known to catalyze the transfer of a geranyl-geranyl moiety from geranylgeranyl pyrophsophate to both cysteines in Rab proteins (Farnsworth, C. C. et al. (1994) *Proc Natl Acad Sci USA* 91(25):11963-11967). Rab proteins are Ras-related small GTPases that are geranylgeranylated on cysteine residues located at or near their C termini. Farnesyltransferase catalyzes the addition of farnesyl groups to the C termini of protein such as Ras.

Mammalian protein geranylgeranyl transferases types 1 and 2 are heterodimers composed of an alpha and beta subunit. The alpha subunit shows homology to the alpha subunits of a closely related enzyme, farnesyltransferase. Farnesyltransferases have been described in pea, tomato, and *Arabidopsis*, but have not been described in monocots (Yang et al. (1993) *Plant Physiology* 101:667-674). Plant farnesyltransferases also consist of alpha and beta subunits. The beta subunit is responsible for peptide-binding and contains a catalytic zinc ion. The beta subunit belongs to the protein prenyltransferase beta subunit family. The geranylgeranyl transferase beta subunit also belongs to the protein prenyltransferase beta subunit family. The beta subunits of the type 1 and 2 geranylgeranyltransferases have not been previously described in plants. Work done in yeast has established that protein geranylgeranyltransferases are distinct from the closely related protein farnesyltransferases.

It has been shown that defects in farnesyltransferase activity enhances plant hormone abscisic acid (ABA) levels. In a normal plant ABA levels increase in response to water deficits. An increase ABA in leaf tissue triggers the closure of leaf stomata to decrease water loss via transpiration (Pei et al. (1998) *Science* 282:287-290). Plants with a decrease in farnesyltransferase activity could confer enhanced tolerance to drought stress in plants. Thus, there is a great deal of interest in identifying the genes that encode farnesyltransferase in plants. These genes may be used in plant cells to control cell growth and produce plants with improved water stress tolerance. Accordingly, the availability of nucleic acid sequences encoding all or a portion of farnesyltransferase proteins would facilitate studies to better understand cell growth in plants, provide genetic tools to control cell growth and improve tolerance to drought in mature plants.

SUMMARY OF THE INVENTION

The present invention relates to isolated polynucleotides comprising a nucleotide sequence encoding a first polypeptide of at least 300 amino acids that has at least 80% identity based on the Clustal method of alignment when compared to a polypeptide selected from the group consisting of a corn farnesyltransferase polypeptide of SEQ ID NO:2, a rice farnesyltransferase polypeptide of SEQ ID NO:4, a soybean farnesyltransferase polypeptide of SEQ ID NO:6, a soybean farnesyltransferase polypeptide of SEQ ID NO:8, a wheat farnesyltransferase polypeptide of SEQ ID NO:10, a corn farnesyltransferase polypeptide of SEQ ID NO:12, a rice farnesyltransferase polypeptide of SEQ ID NO:14, a soybean farnesyltransferase polypeptide of SEQ ID NO:16, and a soybean farnesyltransferase polypeptide of SEQ ID NO:18. The present invention also relates to an isolated polynucleotide comprising the complement of the nucleotide sequences described above. It is preferred that the isolated polynucleotides of the claimed invention consists of regions of the isolated polynucleotide selected from the group consisting of SEQ ID NO:1, 3, 5, 7, 9, 11, 13, 15, and 17 that codes for the polypeptide selected from the group consisting of SEQ ID NO:2, 4, 6, 8, 10, 12, 14, 16 and 18. The present invention also relates to an isolated polynucleotide comprising a nucleotide sequences of at least one of 40 (preferably 30) contiguous nucleotides derived from a nucleotide sequence selected from the group consisting of SEQ ID NO:1, 3, 5, 7, 9, 11, 13, 15, 17 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eucaryotic, such as a yeast or a plant cell, or procaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene or isolated polynucleotide of the present invention, the process comprising either transforming or transfecting an isolated compatible host cell with a chimeric gene or isolated polynucleotide of the present invention.

The present invention relates to a farnesyltransferase polypeptide of at least 300 amino acids that has at least 80% homology based on the Clustal method of alignment compared to a polypeptide selected from the group consisting of SEQ ID NO:2, 4, 6, 8, 10, 12, 14, 16, 18.

The present invention relates to a method of selecting an isolated polynucleotide that affects the level of expression of a farnesyltransferase polypeptide in a plant cell, the method comprising the steps of:

constructing an isolated polynucleotide or chimeric gene of the present invention;
introducing the isolated polynucleotide into a plant cell;
measuring the level of farnesyltransferase polypeptide in the plant cell containing the polynucleotide; and
comparing the level of farnesyltransferase polypeptide in the plant cell containing the isolated polynucleotide with the level of farnesyltransferase polypeptide in a plant cell that does not contain the isolated polynucleotide.

The present invention relates to a method of obtaining a nucleic acid fragment encoding a substantial portion of a farnesyltransferase gene, preferably a plant farnesyltransferase gene, comprising the steps of: synthesizing an oligonucleotide primer comprising a nucleotide sequence of at least one of 40 (preferably 30) contiguous nucleotides derived from a nucleotide sequence selected from the group consisting of SEQ ID NO:1, 3, 5, 7, 9, 11, 13, 15, 17 and the complement of such nucleotide sequences; and amplifying a nucleic acid fragment (preferably a cDNA inserted in a cloning vector) using the oligonucleotide primer. The amplified nucleic acid fragment preferably will encode a portion of a farnesyltransferase polypeptide amino acid sequence.

The present invention also relates to a method of obtaining a nucleic acid fragment encoding all or a substantial portion of the amino acid sequence encoding a farnesyltransferase protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

| Farnesyltransferase Subunits | | | |
|---|---|---|---|
| Protein | Clone Designation | SEQ ID NO: (Nucleotide) | (Amino Acid) |
| Farnesyltransferase Alpha Subunit | cen3n.pk0052.a2 | 1 | 2 |
| Farnesyltransferase Alpha Subunit | rls6.pk0017.g2 | 3 | 4 |
| Farnesyltransferase Alpha Subunit | src1c.pk002.f15 | 5 | 6 |
| Farnesyltransferase Alpha Subunit | sgs2c.pk006.n4 | 7 | 8 |
| Farnesyltransferase Alpha Subunit | Contig composed of: wdk2c.pk013.d24 wr1.pk0110.b1 | 9 | 10 |
| Farnesyltransferase Beta Subunit | p0127.cntbu.18r | 11 | 12 |
| Farnesyltransferase Beta Subunit | rlr24.pk0007.d6 | 13 | 14 |

TABLE 1-continued

| Farnesyltransferase Subunits | | | |
|---|---|---|---|
| Protein | Clone Designation | SEQ ID NO: (Nucleotide) | (Amino Acid) |
| Farnesyltransferase Beta Subunit | sfl1.pk0086.h10 | 15 | 16 |
| Farnesyltransferase Beta Subunit | sgs2c.pk002.g2 | 17 | 18 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-á-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, a polynucleotide comprising a nucleotide sequence of at least one of 40 (preferably 30) contiguous nucleotides derived from a nucleotide sequence selected from the group consisting of SEQ ID NO:1, 3, 5, 7, 9, 11, 13, 15, 17 and the complement of such nucleotide sequences may be used in methods of selecting an isolated polynucleotide that affects the expression of a farnesyltransferase polypeptide in a plant cell.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (polynucleotides) encode amino acid sequences that are 80% identical to the amino acid sequences reported herein. Preferred nucleic acid fragment encode amino acid sequences that are 85% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403-410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several farnesyltransferase subunits have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other farnesyltransferase alpha or beta subunits, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 40 (preferably 30) contiguous nucleotides derived from a nucleotide sequence selected from the group consisting of SEQ ID NO:1, 3, 5, 7, 9, 11, 13, 15, 17 and the complement of such nucleotide sequences may be used in such methods to obtain a nucleic acid fragment encoding a substantial portion of an amino acid sequence of a thioredoxin polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of farnesyltransferase activity in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded farnesyltransferase subunit. An example of a vector for high level expression of the instant polypeptides in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci. USA* 86:9402-9406; Koes et al. (1995) *Proc. Natl. Acad. Sci. USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cen3n | Corn endosperm 20 days after pollination* Corn nucellus tissue, 5 days after silking* | cen3n.pk0052.a2 p0127.cntbu18r |
| rlr24 | Rice leaf 15 days after germination, 24 hours after infection of strain *Magnaporthe grisea* 4360-R-62 (AVR2-YAMO); Resistant | rlr24.pk0007.d6 |
| rls6 | Rice leaf 15 days after germination, 6 hours after infection of *Magnaporthe grisea* strain 4360-R-67 (AVR2-YAMO); susceptible | rls6.pk0017.g2 |
|  |  | sfl1.pk0086.h10 |
| sgs2c | Soybean seeds 14 hours after germination | sgs2c.pk006.n4 |
| sgs2c | Soybean seeds 14 hours after germination | sgs2c.pk002.g2 |
| src1c | Soybean 8 day old root infected with cyst nematode *Heterodera glycinesis* | src1c.pk002.f15 |
| wdk2c | Wheat developing kernel, 7 days after anthesis | wdk2c.pk013.d24 |
| wr1 | Wheat root from 7 day old seedling | wr1.pk0110.b1 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Example 2

Identification of cDNA Clones cDNA clones encoding farnesyltransferase subunits were identified by conducting BLAST (Basic Local Alignment Search Tool; Altschul et al. (1993) *J. Mol. Biol.* 215:403-410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat.*

Genet. 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Farnesyltransferase Alpha Subunits

The BLASTX search using the EST sequences from clones listed in Table 3 revealed similarity of the polypeptides encoded by the cDNAs to farnesyltransferase alpha subunit from *Pisum sativum* (NCBI Identifier No. gi 2246442) and *Arabidopsis thaliana* (NCBI Identifier No. gi 3142698). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides
Homologous to *Pisum sativum* and *Arabidopsis thaliana*
Farnesyltransferase Alpha Subunits

| Clone | Status | BLAST pLog Score |
|---|---|---|
| cen3n.pk0052.a2 | FIS | 115.00 (gi 2246442) |
| rls6.pk0017.g2 | FIS | 121.00 (gi 3142698) |
| src1c.pk002.f15 | FIS | 152.00 (gi 2246442) |
| sgs2c.pk006.n4 | FIS | 150.00 (gi 2246442) |
| Contig composed of:<br>wdk2c.pk013.d24<br>wr1.pk0110.b1 | Contig | 114.00 (gi 3142698) |

The data in Table 4 represents a calculation of the percent identity of the amino acid sequences set forth in SEQ ID NOs:2, 4, 6, 8 and 10 and the *Pisum sativum* and *Arabidopsis thaliana* sequences (SEQ ID NO:19 and 20 respectively). The percent identity between the amino acid sequences set forth in SEQ ID NOs:2, 4, 6, 8 and 10 ranged between 55-99%.

TABLE 4

Percent Identity of Amino Acid Sequences Deduced From
the Nucleotide Sequences of cDNA Clones Encoding Polypeptides
Homologous to *Pisum sativum* and *Arabidopsis thaliana*
Farnesyltransferase Alpha Subunits

| SEQ ID NO. | Percent Identity to |
|---|---|
| 2 | 60% |
| 4 | 62% |
| 6 | 77% |
| 8 | 76% |
| 10 | 62% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a farnesyltransferase alpha subunit. These sequences represent the first corn, rice, soybean and wheat sequences encoding a farnesyltransferase alpha subunit.

Example 4

Characterization of cDNA Clones Encoding Farnesyltransferase Beta Subunits

The BLASTX search using the EST sequences from clones listed in Table 5 revealed similarity of the polypeptides encoded by the cDNAs to farnesyltransferase beta subunit from *Lycopersicon esculentum* (NCBI Identifier No. gi 1815668), *Pisum sativum* (NCBI Identifier No. gi 417482) and *Pisum sativum* (NCBI Identifier No. gi 169049). Shown in Table 5 are the BLAST results for individual ESTs ("EST"), the sequences of the entire cDNA inserts comprising the indicated cDNA clones ("FIS"), or contigs assembled from two or more ESTs ("Contig"):

TABLE 5

BLAST Results for Sequences Encoding Polypeptides
Homologous to *Lycopersicon esculentum* and *Pisum sativum*
Farnesyltransferase Beta Subunits

| Clone | Status | BLAST pLog Score |
|---|---|---|
| p0127.cntbu18r | FIS | 149.00 (gi 1815668) |
| rlr24.pk0007.d6 | FIS | 110.00 (gi 1815668) |
| sfl1.pk0086.h10 | FIS | >254.00 (gi 417482) |
| sgs2c.pk002.g2 | EST | 62.00 (gi 169049) |

The data in Table 6 represents a calculation of the percent identity of the amino acid sequences set forth in SEQ ID NOs:12, 14, 16 and 18 and the *Lycopersicon esculentum* (gi 1815668), *Pisum sativum* (gi 417482) and *Pisum sativum* (gi 169049) sequences. The percent identity between the amino acid sequences set forth in SEQ ID NOs:12, 14, 16 and 18 ranged between 50-81%.

TABLE 6

Percent Identity of Amino Acid Sequences Deduced From
the Nucleotide Sequences of cDNA Clones Encoding Polypeptides
Homologous to *Lycopersicon esculentum* and *Pisum sativum*
Farnesyltransferase Beta Subunits

| SEQ ID NO. | Percent Identity to |
|---|---|
| 12 | 55% |
| 14 | 57% |
| 16 | 77% |
| 18 | 62% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a farnesyltransferase beta subunit. These sequences represent the first corn, rice, soybean and wheat sequences encoding a farnesyltransferase beta subunit.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform $E.$ $coli$ XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810-812) and the 3' region of the nopaline synthase gene from the T-DNA of the Ti plasmid of Agrobacterium tumefaciens.

The particle bombardment method (Klein et al. (1987) Nature 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833-839).

Example 6

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
(a) a nucleotide sequence encoding a polypeptide comprising a farnesyltransferase alpha subunit, wherein the polypeptide has an amino acid sequence of at least 95% sequence identity, based on the Clustal method of alignment with pairwise alignment default parameters of KTUPLE=1, GAP PENALTY=3, WINDOW=5 and DIAGONALS SAVED=5, when compared to SEQ ID NO:6; or
(b) the full length complement of the nucleotide sequence of (a).

2. The polynucleotide of claim 1, wherein the amino acid sequence of the polypeptide comprises SEQ ID NO:6.

3. The polynucleotide of claim 1, wherein the nucleotide sequence comprises SEQ ID NO:5.

4. A vector comprising the polynucleotide of claim 1.

5. A recombinant DNA construct comprising the isolated polynucleotide of claim 1 operably linked to at least one regulatory sequence.

6. A method for transforming a cell, comprising transforming a cell with the recombinant DNA construct of claim 5.

7. A cell comprising the recombinant DNA construct of claim 5, wherein the cell is selected from the group consisting of a bacterial cell, a yeast cell and a plant cell.

8. A method for producing a transgenic plant comprising transforming a plant cell with the recombinant DNA construct of claim 5 and regenerating a transgenic plant from the transformed plant cell.

9. A plant comprising the recombinant DNA construct of claim 5.

10. A seed comprising the recombinant DNA construct of claim 5.

11. A method for isolating a polypeptide encoded by the recombinant DNA construct of claim 5, wherein the method comprises the following:
(a) transforming a cell with the recombinant DNA construct of claim 5;
(b) growing the transformed cell of step (a) under conditions suitable for expression of the recombinant DNA construct; and
(c) isolating the polypeptide from the transformed cell of step (b).

* * * * *

SEQUENCE LISTING

<160> NUMBER OF SEQ ID NOS: 23

<210> SEQ ID NO 1
<211> LENGTH: 1426
<212> TYPE: DNA
<213> ORGANISM: Zea mays

<400> SEQUENCE: 1

```
gcacgagaca gcgcaattac ttaagctatt tgtattcgga tctgatccaa ccctggtggt    60
cagctggact catcgcccat ggagcacact aagtcaggcc ccagcagttg gccagaactg   120
gccgacgtgg tgccggtgcc gcaggacgat gggcctagcc ctgtggtgtc catcgcctat   180
cgagatgact tcgtgaggt catggattac ttccgcgccc tctacctcac cggtgagcga   240
agccctcgcg ctctccgcct caccgccgag gccatcgagc tcaaccccgg caactacact   300
gtctggcatt tccggcgcct tattctggag tcactagatt ttgatttact agaggagatg   360
aaatttgtcg aaaaaattgc tgaatgcaat ccaaaaaatt accaaatctg caccataag    420
agatggcttg ctgagaaatt aggacctggt attgcaaaca aagagcatga attcacaatg   480
aagatacttg ctattgatgc aaaaaattat catgcttggt ctcataggca gtgggttctt   540
caagcgttgg ggggatggga gactgaatta gaatactgtg accacttact taaggaagac   600
gtcttcaata attcagcttg gaatcagaga tactttgtta taacaagatc accatttctt   660
ggtggccttg cggcaatgcg tgattcagaa gtagactaca caattgaagc tattctagca   720
aacgctcaga atgaaagccc tggaggtac ctcaagggtc tatacaaggg tgagaataac   780
ctgctagtag aggacgagcg catctctgct gtttgtttca aggtcctgaa gaatgattgg   840
acttgtgtat ttgctttgag tttgctgctc gatcttctct gcactggttt gcagccttca   900
gatgaactta ggtccactct tgaaacaata aggagctccc atcctgaaac cgcggatgat   960
gatcctgcag ccgctgtttg ctgtatcctg cagaaatgtg atcccctgcg ggtaaattat  1020
tggtcttggt tcaaggacac tctttctcag atctcatgac ttcacatggg ttcacccctt  1080
gtccgcgctg gtccgggctc tgtgagatag acatgtttta gatagtttca ttggacaccc  1140
aaacagagcg gacagagtgt atggctgcta ccttctccgt gactgaaagc agtgcttgta  1200
acgattttgt ttagtaaaat tgtgagtgt tactgctcca acaacacct tatgcaacca   1260
tatttgaata tttcacatgt aagcttgaat ccaggtgtgt ttgttaatgt attacaattg  1320
ccatgggagc ctaaatgaga cccataatca cttccactag agtcggaaga ccgtgtcgag  1380
cagttcactc atatggtcac ttaaagcaaa aaaaaaaaa aaaaaa                  1426
```

<210> SEQ ID NO 2
<211> LENGTH: 326
<212> TYPE: PRT
<213> ORGANISM: Zea mays

<400> SEQUENCE: 2

Met Glu His Thr Lys Ser Gly Pro Ser Ser Trp Pro Glu Leu Ala Asp
 1               5                  10                  15

Val Val Pro Val Pro Gln Asp Asp Gly Pro Ser Pro Val Val Ser Ile
            20                  25                  30

Ala Tyr Arg Asp Asp Phe Arg Glu Val Met Asp Tyr Phe Arg Ala Leu
        35                  40                  45

Tyr Leu Thr Gly Glu Arg Ser Pro Arg Ala Leu Arg Leu Thr Ala Glu
    50                  55                  60

```
Ala Ile Glu Leu Asn Pro Gly Asn Tyr Thr Val Trp His Phe Arg Arg
 65                  70                  75                  80

Leu Ile Leu Glu Ser Leu Asp Phe Asp Leu Leu Glu Glu Met Lys Phe
                 85                  90                  95

Val Glu Lys Ile Ala Glu Cys Asn Pro Lys Asn Tyr Gln Ile Trp His
            100                 105                 110

His Lys Arg Trp Leu Ala Glu Lys Leu Gly Pro Gly Ile Ala Asn Lys
        115                 120                 125

Glu His Glu Phe Thr Met Lys Ile Leu Ala Ile Asp Ala Lys Asn Tyr
    130                 135                 140

His Ala Trp Ser His Arg Gln Trp Val Leu Gln Ala Leu Gly Gly Trp
145                 150                 155                 160

Glu Thr Glu Leu Glu Tyr Cys Asp His Leu Leu Lys Glu Asp Val Phe
                165                 170                 175

Asn Asn Ser Ala Trp Asn Gln Arg Tyr Phe Val Ile Thr Arg Ser Pro
            180                 185                 190

Phe Leu Gly Gly Leu Ala Ala Met Arg Asp Ser Glu Val Asp Tyr Thr
        195                 200                 205

Ile Glu Ala Ile Leu Ala Asn Ala Gln Asn Glu Ser Pro Trp Arg Tyr
    210                 215                 220

Leu Lys Gly Leu Tyr Lys Gly Glu Asn Leu Leu Val Glu Asp Glu
225                 230                 235                 240

Arg Ile Ser Ala Val Cys Phe Lys Val Leu Lys Asn Asp Trp Thr Cys
                245                 250                 255

Val Phe Ala Leu Ser Leu Leu Asp Leu Leu Cys Thr Gly Leu Gln
            260                 265                 270

Pro Ser Asp Glu Leu Arg Ser Thr Leu Glu Thr Ile Arg Ser Ser His
        275                 280                 285

Pro Glu Thr Ala Asp Asp Pro Ala Ala Val Cys Cys Ile Leu
    290                 295                 300

Gln Lys Cys Asp Pro Leu Arg Val Asn Tyr Trp Ser Trp Phe Lys Asp
305                 310                 315                 320

Thr Leu Ser Gln Ile Ser
                325

<210> SEQ ID NO 3
<211> LENGTH: 1218
<212> TYPE: DNA
<213> ORGANISM: Oryza sativa

<400> SEQUENCE: 3
gcacgaggtt ctaacgccgc cgccgccgcc gccgtctccg cagaatctga tcgatggcgc      60
cgtcgtcgac gtcgtcggag ggtgcctccg acgagtggtt gccacccagc cggcggccgg     120
agctggcgga cgtggtcccc gtgacgcagg acgacgggcc ccaccccgtg gtggccatcg     180
cctaccggga cgagttccgc gaggtcatgg actacttccg cgccctctac ttcgccggcg     240
agcgcagcgt ccgcgccctc cacctcaccg ccgaggtcat cgaccttaat cccggcaact     300
acacggtgtg gcattttagg cgtcttgttc tagaggcact ggatgctgat ctgcgtgagg     360
aaatggattt tgtggaccga attgctgaat gtaacccaaa aaattatcaa atctggcatc     420
acaagagatg gcttgcggag aaattaggac agatattgc aaataaagag cacgaattta     480
caaggaagat actttctatg gatgctaaaa attaccatgc ttggtctcat aggcagtggg     540
ttcttcaagc actgggtgga tgggagactg aactacagta ttgcaaccag ctgcttgagg     600
```

-continued

```
aagacgtctt caataattca gcttggaatc agagataccT tgtaataaca agttcaccac    660
ttcttggagg ccttgcagca atgcgtgact cggaagtgga ttacacagtt ggggctattc    720
tggctaaccc tcagaatgaa agccctggag atacctcaa aggcctgtac aagggtgaaa     780
ataacttgct gatggctgat gagcgcatct ctgatgtttg tctcaaggtc ctgaaacatg    840
attcgacctg cgtatttgct ttgagcttgc tgctcgatct tcttcaaatt ggtttacaac    900
cttcagatga actcaaagga actatcgaag caataaagaa ctctgatcct gaagcagatg    960
aagcagtaga tgctgatctt gcgactgcaa tctgctcaat attgcagaga tgtgatcccc   1020
tgcggataaa ttactggtcc tggtacagga ccactatttc ttctcaaacc tgaagcatgc   1080
agtggcctcc atgaggtcat aatggagata tcttctatct tcgtgtgatt ctgggcgttg   1140
aggtgcctag ctacatttgt tatgaacttt ccttgggcat aactgatcac tgatatattact 1200 ccaatattgt gttctaaa                                                 1218
```

<210> SEQ ID NO 4
<211> LENGTH: 339
<212> TYPE: PRT
<213> ORGANISM: Oryza sativa

<400> SEQUENCE: 4

```
Met Ala Pro Ser Ser Thr Ser Ser Glu Gly Ala Ser Asp Glu Trp Leu
  1               5                  10                  15

Pro Pro Ser Arg Arg Pro Glu Leu Ala Asp Val Val Pro Val Thr Gln
             20                  25                  30

Asp Asp Gly Pro His Pro Val Val Ala Ile Ala Tyr Arg Asp Glu Phe
         35                  40                  45

Arg Glu Val Met Asp Tyr Phe Arg Ala Leu Tyr Phe Ala Gly Glu Arg
     50                  55                  60

Ser Val Arg Ala Leu His Leu Thr Ala Glu Val Ile Asp Leu Asn Pro
 65                  70                  75                  80

Gly Asn Tyr Thr Val Trp His Phe Arg Arg Leu Val Leu Glu Ala Leu
                 85                  90                  95

Asp Ala Asp Leu Arg Glu Glu Met Asp Phe Val Asp Arg Ile Ala Glu
            100                 105                 110

Cys Asn Pro Lys Asn Tyr Gln Ile Trp His His Lys Arg Trp Leu Ala
        115                 120                 125

Glu Lys Leu Gly Pro Asp Ile Ala Asn Lys Glu His Glu Phe Thr Arg
    130                 135                 140

Lys Ile Leu Ser Met Asp Ala Lys Asn Tyr His Ala Trp Ser His Arg
145                 150                 155                 160

Gln Trp Val Leu Gln Ala Leu Gly Gly Trp Glu Thr Glu Leu Gln Tyr
                165                 170                 175

Cys Asn Gln Leu Leu Glu Glu Asp Val Phe Asn Asn Ser Ala Trp Asn
            180                 185                 190

Gln Arg Tyr Leu Val Ile Thr Ser Ser Pro Leu Leu Gly Gly Leu Ala
        195                 200                 205

Ala Met Arg Asp Ser Glu Val Asp Tyr Thr Val Gly Ala Ile Leu Ala
    210                 215                 220

Asn Pro Gln Asn Glu Ser Pro Trp Arg Tyr Leu Lys Gly Leu Tyr Lys
225                 230                 235                 240

Gly Glu Asn Asn Leu Leu Met Ala Asp Glu Arg Ile Ser Asp Val Cys
                245                 250                 255
```

```
Leu Lys Val Leu Lys His Asp Ser Thr Cys Val Phe Ala Leu Ser Leu
            260                 265                 270

Leu Leu Asp Leu Leu Gln Ile Gly Leu Gln Pro Ser Asp Glu Leu Lys
        275                 280                 285

Gly Thr Ile Glu Ala Ile Lys Asn Ser Asp Pro Glu Ala Asp Glu Ala
    290                 295                 300

Val Asp Ala Asp Leu Ala Thr Ala Ile Cys Ser Ile Leu Gln Arg Cys
305                 310                 315                 320

Asp Pro Leu Arg Ile Asn Tyr Trp Ser Trp Tyr Arg Thr Thr Ile Ser
                325                 330                 335

Ser Gln Thr

<210> SEQ ID NO 5
<211> LENGTH: 1261
<212> TYPE: DNA
<213> ORGANISM: Glycine max

<400> SEQUENCE: 5
gcacgaggat taacgaagga tggaatctgg gtctagcgaa ggagaagagg tgcagcaacg      60
cgtgccgttg agggagagag tggagtggtc agatgttact ccggttcctc aaaacgacgg     120
ccctaaccct gtcgttccga tccagtacac tgaagagttt tccgaagtta tggattactt     180
tcgcgccgtt tacctcaccg atgaacgctc ccctcgcgcc ctcgctctca cagccgaagc     240
cgttcaattc aactccggca actacactgt gtggcatttc cgacggttgt tacttgagtc     300
gctaaaagtc gacttgaacg atgaactgga ttttgtggag cgtatggccg ctggaaattc     360
taaaaattat cagatgtggc atcatagacg atgggttgcc gagaagttag gtcctgaagc     420
tagaaacaat gagctcgagt tcaccaaaaa gatactgtcc gttgatgcca acattatca     480
tgcatggtct catagacagt gggctcttca aacactagga ggatgggaag atgaacttaa     540
ttattgcaca gaactactta agaagacat ttttaacaat tctgcttgga atcagagata     600
ttttgtcata acaaggtctc ctttcttggg gggcctaaaa gctatgagag agtctgaagt     660
gctttacacc attgaagcca ttatagccta ccctgaaaat gaaagctcgt ggagatatct     720
acgaggactt tataaaggtg aaactacttc atgggtaaat gatcctcaag tttcttcagt     780
atgcttaaag attttgagaa ctaagagcaa ctacgtgttt gctcttagca ctattttaga     840
tcttatatgc tttggttatc aaccaaatga agacattaga gatgccattg acgccttaaa     900
gaccgcagat atggataaac aagatttaga tgatgatgag aaaggggaac aacaaaattt     960
aaatatagca cgaaatattt gttctatcct aaaacaagtt gatccaatta gaaccaacta    1020
ttggatttgg cgcaagagca gacttcctct atcagcttag taaccaaagt aattaaaggg    1080
caactctgtg ttatgtgtaa cctagtttat tgaaactgga ttttattta ttattatttt    1140
ttatgttgtc atgtatctgt ttgtgcaaat ttatcttttt gtcatgccat tactggcatt    1200
tgagtgtaag gattgaaagc catgcagaat aagaaattta agttttttt tccgttgaaa    1260
a                                                                   1261

<210> SEQ ID NO 6
<211> LENGTH: 346
<212> TYPE: PRT
<213> ORGANISM: Glycine max

<400> SEQUENCE: 6

Met Glu Ser Gly Ser Ser Glu Gly Glu Glu Val Gln Gln Arg Val Pro
  1               5                   10                  15
```

Leu Arg Glu Arg Val Glu Trp Ser Asp Val Thr Pro Val Pro Gln Asn
            20                  25                  30

Asp Gly Pro Asn Pro Val Val Pro Ile Gln Tyr Thr Glu Glu Phe Ser
            35                  40                  45

Glu Val Met Asp Tyr Phe Arg Ala Val Tyr Leu Thr Asp Glu Arg Ser
        50                  55                  60

Pro Arg Ala Leu Ala Leu Thr Ala Glu Ala Val Gln Phe Asn Ser Gly
65                  70                  75                  80

Asn Tyr Thr Val Trp His Phe Arg Arg Leu Leu Leu Glu Ser Leu Lys
                85                  90                  95

Val Asp Leu Asn Asp Glu Leu Asp Phe Val Glu Arg Met Ala Ala Gly
            100                 105                 110

Asn Ser Lys Asn Tyr Gln Met Trp His His Arg Arg Trp Val Ala Glu
            115                 120                 125

Lys Leu Gly Pro Glu Ala Arg Asn Asn Glu Leu Glu Phe Thr Lys Lys
        130                 135                 140

Ile Leu Ser Val Asp Ala Lys His Tyr His Ala Trp Ser His Arg Gln
145                 150                 155                 160

Trp Ala Leu Gln Thr Leu Gly Gly Trp Glu Asp Glu Leu Asn Tyr Cys
                165                 170                 175

Thr Glu Leu Leu Lys Glu Asp Ile Phe Asn Asn Ser Ala Trp Asn Gln
            180                 185                 190

Arg Tyr Phe Val Ile Thr Arg Ser Pro Phe Leu Gly Gly Leu Lys Ala
            195                 200                 205

Met Arg Glu Ser Glu Val Leu Tyr Thr Ile Glu Ala Ile Ala Tyr
        210                 215                 220

Pro Glu Asn Glu Ser Ser Trp Arg Tyr Leu Arg Gly Leu Tyr Lys Gly
225                 230                 235                 240

Glu Thr Thr Ser Trp Val Asn Asp Pro Gln Val Ser Ser Val Cys Leu
                245                 250                 255

Lys Ile Leu Arg Thr Lys Ser Asn Tyr Val Phe Ala Leu Ser Thr Ile
            260                 265                 270

Leu Asp Leu Ile Cys Phe Gly Tyr Gln Pro Asn Glu Asp Ile Arg Asp
            275                 280                 285

Ala Ile Asp Ala Leu Lys Thr Ala Asp Met Asp Lys Gln Asp Leu Asp
        290                 295                 300

Asp Asp Glu Lys Gly Glu Gln Gln Asn Leu Asn Ile Ala Arg Asn Ile
305                 310                 315                 320

Cys Ser Ile Leu Lys Gln Val Asp Pro Ile Arg Thr Asn Tyr Trp Ile
                325                 330                 335

Trp Arg Lys Ser Arg Leu Pro Leu Ser Ala
            340                 345

<210> SEQ ID NO 7
<211> LENGTH: 1333
<212> TYPE: DNA
<213> ORGANISM: Glycine max

<400> SEQUENCE: 7
gcacgagctt gcgtgtggag tgaagaagat taacgaagga tggaatctgg gtctagcgaa      60
ggagaagagg tgcagcaacg cgtgccgttg agggagagag tggagtggtc agatgttact     120
ccggttcctc aaaacgacgg ccctaaccct gtcgttccga tccagtacac tgaagagttt     180
tccgaagtta tggattactt tcgcgccgtt tacctcaccg atgaacgctc ccctcgcgcc     240

```
ctcgctctca cagccgaagc cgttcaattc aactccggca actacactgt gtggcatttc    300
cgacggttgt tacttgagtc gctaaaagtc gacttgaacg atgaactgga gtttgtggag    360
cgtatggccg ctggaaattc taaaaattat cagatgtggt gtgatgctct gctctgctct    420
ttcttccata ctttgcatca tagacgatgg gttgccgaga agttaggtcc tgaagctaga    480
aacaatgagc tcgagttcac caaaaagata ctgtccgttg atgccaaaca ttatcatgca    540
tggtctcata gacagtgggc tcttcaaaca ctaggaggat gggaagatga acttaattat    600
tgcacagaac tacttaaaga agacattttt aacaattctg cttggaatca gagatatttt    660
gtcataacaa ggtctccttt cttgggggc ctaaaagcta tgagagagtc tgaagtgctt    720
tacaccattg aagccattat agcctaccct gaaaatgaaa gctcgtggag atatctacga    780
ggactttata aaggtgaaac tacttcatgg gtaaatgatc ctcaagtttc ttcagtatgc    840
ttaaagattt tgagaactaa gagcaactac gtgtttgctc ttagcactat tttagatctt    900
atatgctttg gttatcaacc aaatgaagac attagagatg ccattgacgc cttaaagacc    960
gcagatatgg ataaacaaga tttagatgat gatgagaaag gggaacaaca aaatttaaat   1020
atagcacgaa atatttgttc tatcctaaaa caagttgatc caattagaac caactattgg   1080
atttggcgca agagcagact tcctctatca gcttagtaac caaagtaatt aaagggcaac   1140
tctgtgttat gtgtaaccta gtttattgaa actggatgtt tatttattat tattttttat   1200
gttgtcatgt atctgtttgt gcaaatttat cttttttgtca tgccattact ggcatttgag   1260
tgtaaggatt gaaagccatg cagaataaga aatttaagtt ttttttttccg ttgaaaaaaa   1320
aaaaaaaaaa aaa                                                       1333
```

<210> SEQ ID NO 8
<211> LENGTH: 358
<212> TYPE: PRT
<213> ORGANISM: Glycine max

<400> SEQUENCE: 8

```
Met Glu Ser Gly Ser Ser Glu Gly Glu Glu Val Gln Gln Arg Val Pro
  1               5                  10                  15

Leu Arg Glu Arg Val Glu Trp Ser Asp Val Thr Pro Val Pro Gln Asn
             20                  25                  30

Asp Gly Pro Asn Pro Val Val Pro Ile Gln Tyr Thr Glu Glu Phe Ser
         35                  40                  45

Glu Val Met Asp Tyr Phe Arg Ala Val Tyr Leu Thr Asp Glu Arg Ser
     50                  55                  60

Pro Arg Ala Leu Ala Leu Thr Ala Glu Ala Val Gln Phe Asn Ser Gly
 65                  70                  75                  80

Asn Tyr Thr Val Trp His Phe Arg Arg Leu Leu Leu Glu Ser Leu Lys
                 85                  90                  95

Val Asp Leu Asn Asp Glu Leu Glu Phe Val Glu Arg Met Ala Ala Gly
            100                 105                 110

Asn Ser Lys Asn Tyr Gln Met Trp Cys Asp Ala Leu Leu Cys Ser Phe
        115                 120                 125

Phe His Thr Leu His His Arg Arg Trp Val Ala Glu Lys Leu Gly Pro
    130                 135                 140

Glu Ala Arg Asn Asn Glu Leu Glu Phe Thr Lys Lys Ile Leu Ser Val
145                 150                 155                 160

Asp Ala Lys His Tyr His Ala Trp Ser His Arg Gln Trp Ala Leu Gln
                165                 170                 175
```

```
Thr Leu Gly Gly Trp Glu Asp Glu Leu Asn Tyr Cys Thr Glu Leu Leu
            180                 185                 190

Lys Glu Asp Ile Phe Asn Asn Ser Ala Trp Asn Gln Arg Tyr Phe Val
        195                 200                 205

Ile Thr Arg Ser Pro Phe Leu Gly Gly Leu Lys Ala Met Arg Glu Ser
    210                 215                 220

Glu Val Leu Tyr Thr Ile Glu Ala Ile Ile Ala Tyr Pro Glu Asn Glu
225                 230                 235                 240

Ser Ser Trp Arg Tyr Leu Arg Gly Leu Tyr Lys Gly Glu Thr Thr Ser
                245                 250                 255

Trp Val Asn Asp Pro Gln Val Ser Ser Val Cys Leu Lys Ile Leu Arg
            260                 265                 270

Thr Lys Ser Asn Tyr Val Phe Ala Leu Ser Thr Ile Leu Asp Leu Ile
        275                 280                 285

Cys Phe Gly Tyr Gln Pro Asn Glu Asp Ile Arg Asp Ala Ile Asp Ala
    290                 295                 300

Leu Lys Thr Ala Asp Met Asp Lys Gln Asp Leu Asp Asp Glu Lys
305                 310                 315                 320

Gly Glu Gln Gln Asn Leu Asn Ile Ala Arg Asn Ile Cys Ser Ile Leu
                325                 330                 335

Lys Gln Val Asp Pro Ile Arg Thr Asn Tyr Trp Ile Trp Arg Lys Ser
            340                 345                 350

Arg Leu Pro Leu Ser Ala
        355

<210> SEQ ID NO 9
<211> LENGTH: 1339
<212> TYPE: DNA
<213> ORGANISM: Triticum aestivum

<400> SEQUENCE: 9
cggacgtggc gccgctgccg caggccgacg ggccctgccc cgtcgtctcc atcgcttacc      60
gcggcgactt ccgcgaggtc atggactact tccgcgccct ctacgccgcc ggcgagcgca     120
gccccgcgc cctccgcctc accgccgacg ccatccacct caaccccggc aactacactg     180
tatgcattt caggcgcgtt gttctagagg cactggatgc tgattattg ctagaaatgc     240
attttgtgga ccaaattgct gaatctaatc aaaaaatta ccagtctgg catcacaaga     300
gatggcttgc tgagaaaata ggaccagatg ctgcaaatag tgaacatgac ttcacaagga     360
agatacttgc tatggatgct aaaaactacc atgcttggtc ccataggcag tgggttcttc     420
aagcattggg tggatgggag agtgaactgc agtactgcaa ccagcttctt gaggaagatg     480
tcttcaataa ctcagcttgg aatcagagat accttgtggt aacacgatca ccaattcttg     540
ggggccttgc ggcaatgcgc gactcagaag tagattacac agttgaggcc attatggtga     600
accctcagaa tgaaagcccc tggagatacc tcagaggttt atataaggat gataacaatt     660
tgctggtggc tgataatcgc atttctgatg cttgcctcaa ggtcctgaat aaggattgga     720
catgcgtatt tgctttgagc ttcctgcttg atcttcttcg catgggtttg cagccttcga     780
atgaacttaa ggaaccatc gaagcaatgg agaactctga tcctgaaacg ggacatgctg     840
atattgcagt agctgtctgc tcaatcctgc agaaatgtga tccctgcgg ataaactact     900
ggtcatggta ccagaccact ctttcttctt agacatctga aaattcagct gaagacagtt     960
ttagcagcat gatgtaaact caatcgaagg ggttgacgca gtgtatgaaa aacctttcct    1020
```

```
gtgatcttgg tgcggagcaa tttgtactga ttttactggg aaaaatcaat caatgacagc   1080
atgcccaaca atgtcttgtg tgaatatgtt actgcctgat attcacatgt tagcagaatg   1140
agaataacca atcaaactcc aacgagcaga ttgttacagt aacggccact ggtggtgtga   1200
aaatcctgaa atctgcttca gtcactttgc cttgtttaca gttgagtctg ttgttgtgat   1260
ctgtacctaa tgcatgtaca caatcatcaa attattagtt tttgtaccaa tgagtattcg   1320
atgaaaaaaa aaaaaaaaa                                                1339
```

<210> SEQ ID NO 10
<211> LENGTH: 309
<212> TYPE: PRT
<213> ORGANISM: Triticum aestivum

<400> SEQUENCE: 10

```
Asp Val Ala Pro Leu Pro Gln Ala Asp Gly Pro Cys Pro Val Val Ser
  1               5                  10                  15

Ile Ala Tyr Arg Gly Asp Phe Arg Glu Val Met Asp Tyr Phe Arg Ala
             20                  25                  30

Leu Tyr Ala Ala Gly Glu Arg Ser Pro Arg Ala Leu Arg Leu Thr Ala
         35                  40                  45

Asp Ala Ile His Leu Asn Pro Gly Asn Tyr Thr Val Trp His Phe Arg
     50                  55                  60

Arg Val Val Leu Glu Ala Leu Asp Ala Asp Leu Leu Glu Met His
 65                  70                  75                  80

Phe Val Asp Gln Ile Ala Glu Ser Asn Pro Lys Asn Tyr Gln Val Trp
                 85                  90                  95

His His Lys Arg Trp Leu Ala Glu Lys Ile Gly Pro Asp Ala Ala Asn
            100                 105                 110

Ser Glu His Asp Phe Thr Arg Lys Ile Leu Ala Met Asp Ala Lys Asn
        115                 120                 125

Tyr His Ala Trp Ser His Arg Gln Trp Val Leu Gln Ala Leu Gly Gly
    130                 135                 140

Trp Glu Ser Glu Leu Gln Tyr Cys Asn Gln Leu Leu Glu Glu Asp Val
145                 150                 155                 160

Phe Asn Asn Ser Ala Trp Asn Gln Arg Tyr Leu Val Val Thr Arg Ser
                165                 170                 175

Pro Ile Leu Gly Gly Leu Ala Ala Met Arg Asp Ser Glu Val Asp Tyr
            180                 185                 190

Thr Val Glu Ala Ile Met Val Asn Pro Gln Asn Glu Ser Pro Trp Arg
        195                 200                 205

Tyr Leu Arg Gly Leu Tyr Lys Asp Asp Asn Leu Leu Val Ala Asp
    210                 215                 220

Asn Arg Ile Ser Asp Ala Cys Leu Lys Val Leu Asn Lys Asp Trp Thr
225                 230                 235                 240

Cys Val Phe Ala Leu Ser Phe Leu Leu Asp Leu Arg Met Gly Leu
                245                 250                 255

Gln Pro Ser Asn Glu Leu Lys Gly Thr Ile Glu Ala Met Glu Asn Ser
            260                 265                 270

Asp Pro Glu Thr Gly His Ala Asp Ile Ala Val Ala Val Cys Ser Ile
        275                 280                 285

Leu Gln Lys Cys Asp Pro Leu Arg Ile Asn Tyr Trp Ser Trp Tyr Gln
    290                 295                 300

Thr Thr Leu Ser Ser
305
```

<210> SEQ ID NO 11
<211> LENGTH: 1359
<212> TYPE: DNA
<213> ORGANISM: Zea mays

<400> SEQUENCE: 11

```
atggacccct ccccgcagtc gacgccgccc accggagacg acccggcagc ggcggcggat     60
cccgacctac cgaggctcac ggtgacgcag gtggagcaga tgaaggtgga ggccagggtt    120
ggcgacatct accgctccct cttcggggcc gcgcccaaca cgaaatccat catgctagag    180
ctgtggcgtg atcagcatat cgagtatctg acgcctgggc tgaggcatat gggaccagcc    240
tttcatgttc tagatgccaa tcgcccttgg ctatgctact ggatggttca tccacttgct    300
ttgctggatg aagcacttga tgatgatctt gagaatgata tcatagactt cttagctcga    360
tgtcaggata agatggtgg atatagtggt ggacctggac agttgcctca cctagctacg    420
acttatgctg ctgtaaatac acttgtgaca atagggagcg aaagagcatt gtcatcaatc    480
aatagggca acctgtacaa ttttatgctg cagatgaaag atgtatcagg tgctttcaga    540
atgcatgatg gtggcgaaat tgatgtccgt gcttcctaca ccgctatatc ggttgccagc    600
cttgtgaata ttcttgattt taaactggca aaggtgtag gcgactacat agcaagatgt    660
caaacttatg aaggtggtat tgctggggag ccttatgctg aagcacatgg tgggtataca    720
ttctgtggat tggctgcttt gatcctgctt aatgaggcag agaaagttga cttgcctagt    780
ttgattggct gggtggcttt tcgtcaagga gtggaatgcg gatttcaagg acgaactaat    840
aaattggttg atggttgcta ctccttttgg cagggagctg ccattgcttt cacacaaaag    900
ttaattacga ttgttgataa gcaattgaag tcctcgtatt cctgcaaaag gccatcagga    960
gaggatgcct gcagcaccag ttcatatggg tgcaccgcga aaaagtcttc ctctgctgtg   1020
gactatgcga agtttggatt tgattttata acagagca accaaattgg cccactcttc   1080
cataacattg ccctgcaaca atacatccta ctttgttctc aggtactaga gggaggcttg   1140
agggataagc ctggaaagaa cagagatcac tatcattcat gctactgcct cagtggcctc   1200
gcagttagcc agtacagtgc catgactgat actggttcgt gcccattacc tcagcatgtg   1260
cttggaccgt actctaattt gctggagcca atccatccac tctacaatgt tgtcctagat   1320
aagtaccata cagcctatga gttcttctca gaagagtga                          1359
```

<210> SEQ ID NO 12
<211> LENGTH: 452
<212> TYPE: PRT
<213> ORGANISM: Zea mays

<400> SEQUENCE: 12

```
Met Asp Pro Ser Pro Gln Ser Thr Pro Pro Thr Gly Asp Asp Pro Ala
 1               5                  10                  15

Ala Ala Ala Asp Pro Asp Leu Pro Arg Leu Thr Val Thr Gln Val Glu
            20                  25                  30

Gln Met Lys Val Glu Ala Arg Val Gly Asp Ile Tyr Arg Ser Leu Phe
        35                  40                  45

Gly Ala Ala Pro Asn Thr Lys Ser Ile Met Leu Glu Leu Trp Arg Asp
    50                  55                  60

Gln His Ile Glu Tyr Leu Thr Pro Gly Leu Arg His Met Gly Pro Ala
65                  70                  75                  80

Phe His Val Leu Asp Ala Asn Arg Pro Trp Leu Cys Tyr Trp Met Val
```

-continued

```
                    85                  90                  95
His Pro Leu Ala Leu Leu Asp Glu Ala Leu Asp Asp Leu Glu Asn
                100                 105                 110
Asp Ile Ile Asp Phe Leu Ala Arg Cys Gln Asp Lys Asp Gly Gly Tyr
            115                 120                 125
Ser Gly Gly Pro Gly Gln Leu Pro His Leu Ala Thr Thr Tyr Ala Ala
    130                 135                 140
Val Asn Thr Leu Val Thr Ile Gly Ser Glu Arg Ala Leu Ser Ser Ile
145                 150                 155                 160
Asn Arg Gly Asn Leu Tyr Asn Phe Met Leu Gln Met Lys Asp Val Ser
                165                 170                 175
Gly Ala Phe Arg Met His Asp Gly Gly Glu Ile Asp Val Arg Ala Ser
                180                 185                 190
Tyr Thr Ala Ile Ser Val Ala Ser Leu Val Asn Ile Leu Asp Phe Lys
            195                 200                 205
Leu Ala Lys Gly Val Gly Asp Tyr Ile Ala Arg Cys Gln Thr Tyr Glu
    210                 215                 220
Gly Gly Ile Ala Gly Glu Pro Tyr Ala Glu Ala His Gly Gly Tyr Thr
225                 230                 235                 240
Phe Cys Gly Leu Ala Ala Leu Ile Leu Leu Asn Glu Ala Glu Lys Val
                245                 250                 255
Asp Leu Pro Ser Leu Ile Gly Trp Val Ala Phe Arg Gln Gly Val Glu
                260                 265                 270
Cys Gly Phe Gln Gly Arg Thr Asn Lys Leu Val Asp Gly Cys Tyr Ser
            275                 280                 285
Phe Trp Gln Gly Ala Ala Ile Ala Phe Thr Gln Lys Leu Ile Thr Ile
    290                 295                 300
Val Asp Lys Gln Leu Lys Ser Ser Tyr Ser Cys Lys Arg Pro Ser Gly
305                 310                 315                 320
Glu Asp Ala Cys Ser Thr Ser Ser Tyr Gly Cys Thr Ala Lys Lys Ser
                325                 330                 335
Ser Ser Ala Val Asp Tyr Ala Lys Phe Gly Phe Asp Phe Ile Gln Gln
            340                 345                 350
Ser Asn Gln Ile Gly Pro Leu Phe His Asn Ile Ala Leu Gln Gln Tyr
    355                 360                 365
Ile Leu Leu Cys Ser Gln Val Leu Glu Gly Gly Leu Arg Asp Lys Pro
370                 375                 380
Gly Lys Asn Arg Asp His Tyr His Ser Cys Tyr Cys Leu Ser Gly Leu
385                 390                 395                 400
Ala Val Ser Gln Tyr Ser Ala Met Thr Asp Thr Gly Ser Cys Pro Leu
                405                 410                 415
Pro Gln His Val Leu Gly Pro Tyr Ser Asn Leu Leu Glu Pro Ile His
                420                 425                 430
Pro Leu Tyr Asn Val Val Leu Asp Lys Tyr His Thr Ala Tyr Glu Phe
            435                 440                 445
Phe Ser Glu Glu
    450
```

<210> SEQ ID NO 13
<211> LENGTH: 1031
<212> TYPE: DNA
<213> ORGANISM: Oryza sativa

<400> SEQUENCE: 13

```
gcacgagggc gtagccgcct ttcggtgaga tccccgcggc tgcagcgagc tcgcaggccg      60
ccgccttccg cgccgccgac caccgcgccc atggaccccc cctcgccgcc gccgccgccg     120
ccatatcctc ctgctgctgc tgagggcggt ccggcagcgg atagccaggc cgctgagctg     180
ccccggctga ctgtgacgca ggtggagcag atgaaggtgg aggcgaaggt gggcgaaatc     240
taccgcgtcc tcttcggcaa cgcgcccaac gccaattccc tcatgttaga gctgtggcgt     300
gagcagcatg ttgagtattt gacgagaggg ctgaaacatc ttggaccaag cttccatgtg     360
ctcgatgcca atcgaccttg gctgtgctac tggattattc atgcacttgc tctgttggat     420
gaaatacctg acgatgttga ggatgatatt gtggacttct tatctcgatg tcaggacaaa     480
gatggtggtt atggcggagg acctggacag ttgcctcatc tcgctacaac ttatgctgct     540
gtaaatacac ttgtaactat agggagtgaa agggcactat catcggtaaa cagggacaac     600
ctgtacaagt tcatgcttcg gatgaaagat acatcgggag ctttcagaat gcatgatggt     660
ggtgaaatag atgttcgtgc tagctatact gcaatatcgg ttgccagcct tgtgaacatt     720
cttgatggtg aactagcaaa aggtgttgga aattacataa caaggtgtca aacctatgaa     780
ggtggcattg ctggggaacc gtatgctgaa gctcatggtg gtacacttt tgtgggctg      840 gctacgatga tcctgcttaa cgaagtggac aaacttgatt tggctagctt gattggctgg     900
gtggcatttc gccaaggagt ggaatgtgga tttcaaggac gaactaataa attggttgat     960
ggttgctact ccttttggca gggagctgct cttgctttaa ctgttcaccg cgtggcgccg    1020
actgccaaac g                                                         1031

<210> SEQ ID NO 14
<211> LENGTH: 313
<212> TYPE: PRT
<213> ORGANISM: Oryza sativa

<400> SEQUENCE: 14

Met Asp Pro Pro Ser Pro Pro Pro Pro Tyr Pro Pro Ala Ala
  1               5                  10                  15

Ala Glu Gly Gly Pro Ala Ala Asp Ser Gln Ala Ala Glu Leu Pro Arg
             20                  25                  30

Leu Thr Val Thr Gln Val Glu Gln Met Lys Val Glu Ala Lys Val Gly
         35                  40                  45

Glu Ile Tyr Arg Val Leu Phe Gly Asn Ala Pro Asn Ala Asn Ser Leu
     50                  55                  60

Met Leu Glu Leu Trp Arg Glu Gln His Val Glu Tyr Leu Thr Arg Gly
 65                  70                  75                  80

Leu Lys His Leu Gly Pro Ser Phe His Val Leu Asp Ala Asn Arg Pro
                 85                  90                  95

Trp Leu Cys Tyr Trp Ile Ile His Ala Leu Ala Leu Leu Asp Glu Ile
            100                 105                 110

Pro Asp Asp Val Glu Asp Asp Ile Val Asp Phe Leu Ser Arg Cys Gln
        115                 120                 125

Asp Lys Asp Gly Gly Tyr Gly Gly Pro Gly Gln Leu Pro His Leu
    130                 135                 140

Ala Thr Thr Tyr Ala Ala Val Asn Thr Leu Val Thr Ile Gly Ser Glu
145                 150                 155                 160

Arg Ala Leu Ser Ser Val Asn Arg Asp Asn Leu Tyr Lys Phe Met Leu
                165                 170                 175

Arg Met Lys Asp Thr Ser Gly Ala Phe Arg Met His Asp Gly Gly Glu
            180                 185                 190
```

```
Ile Asp Val Arg Ala Ser Tyr Thr Ala Ile Ser Val Ala Ser Leu Val
            195                 200                 205

Asn Ile Leu Asp Gly Glu Leu Ala Lys Gly Val Gly Asn Tyr Ile Thr
        210                 215                 220

Arg Cys Gln Thr Tyr Glu Gly Gly Ile Ala Gly Glu Pro Tyr Ala Glu
225                 230                 235                 240

Ala His Gly Gly Tyr Thr Phe Cys Gly Leu Ala Thr Met Ile Leu Leu
                245                 250                 255

Asn Glu Val Asp Lys Leu Asp Leu Ala Ser Leu Ile Gly Trp Val Ala
            260                 265                 270

Phe Arg Gln Gly Val Glu Cys Gly Phe Gln Gly Arg Thr Asn Lys Leu
        275                 280                 285

Val Asp Gly Cys Tyr Ser Phe Trp Gln Gly Ala Ala Leu Ala Leu Thr
290                 295                 300

Val His Arg Val Ala Pro Thr Ala Lys
305                 310

<210> SEQ ID NO 15
<211> LENGTH: 1504
<212> TYPE: DNA
<213> ORGANISM: Glycine max

<400> SEQUENCE: 15
gcacgaggac aaatccgccg ccgccgccgc cgtgtccgac ggtgagtcaa cgtgagcaat     60
ggatggtaga gtcgcaggtg tttcagattt accaactctt cgccaccatt cctcgcaacg    120
cccaaaccct catgttggag cttcaacgcg ataatcacat gcagtatgtc tccaaaggcc    180
ttcgccatct cagttccgca ttttccgttt tggacgctaa tcgaccctgg ctctgctact    240
ggatcttcca ctccattgct ttgtcggag aatccgtcga tgatgaactc gaagataacg     300
ctatcgattt tcttaaccgt tgccaggatc cgaatggtgg atatgccggg ggaccaggcc    360
agatgcctca tattgccaca acttatgctg ctgttaattc acttattact ttgggtggtg    420
agaaatccct ggcatcaatt aatagagata aactgtatgg gtttctgcgg cggatgaagc    480
aaccaaatgg tggattcagg atgcatgatg aaggtgaaat tgatgttcga gcttgctaca    540
ctgccatttc tgttgcaagt gttttgaaca ttttggatga tgagctgatc cagaatgttg    600
agactacat tataagctgt caaacatatg agggtggcat tgctggtgag cctggttctg     660
aggctcatgg tgggtacacc ttttgtggat tagctacaat gattctgatt ggtgaggtta    720
atcacttgga tctgcctcga ttagttgact gggtggtatt ccgacaaggt aaggaatgtg    780
gattccaggg gagaacaaat aaactggtgg atggatgcta ttccttttgg cagggaggtg    840
ctgttgctct attgcaaaga ttatcttcta ttatcaacaa acagatggaa gagacatcac    900
agattttgc ggtatcttat gtatctgaag caaaagaaag tttggatgga acctctagtc     960
atgcaacatg ccgtggtgag catgaaggca ccagtgaatc cagttcatct gattttaaaa   1020
atattgccta taaatttatt aatgagtgga gagcacaaga accactttt cacagtattg    1080
ctttacagca atatattctc ttatgtgcac aggagcaaga gggtggactg agagacaaac   1140
cgggtaaacg tagagatcat tatcacacat gttactgttt aagtggactc tcattgtgcc   1200
agtatagttg gtcaaagcac ccagattctc caccactgcc taatctagta ttaggcccct   1260
actctaatct cttagaacca atccacccc tctttaatgt tgtcttggga cgatatcgtg    1320
aagctcatga attcttcttt actgagtcgt gaccactggt tttagctacc aacaacttta   1380
```

```
tttgtataat gtaaataaa ttcattggaa catataaatg taaaacagca ttggattaaa      1440
aaaaaaaaaa aaaaaaaaaa aaaaaaaaaa aaaaaaaaaa aaaaaaaaaa aaaaaaaaaa      1500
aaaa                                                                   1504
```

<210> SEQ ID NO 16
<211> LENGTH: 429
<212> TYPE: PRT
<213> ORGANISM: Glycine max

<400> SEQUENCE: 16

```
Met Val Glu Ser Gln Val Phe Gln Ile Tyr Gln Leu Phe Ala Thr Ile
 1               5                  10                  15

Pro Arg Asn Ala Gln Thr Leu Met Leu Glu Leu Gln Arg Asp Asn His
                20                  25                  30

Met Gln Tyr Val Ser Lys Gly Leu Arg His Leu Ser Ser Ala Phe Ser
        35                  40                  45

Val Leu Asp Ala Asn Arg Pro Trp Leu Cys Tyr Trp Ile Phe His Ser
    50                  55                  60

Ile Ala Leu Ser Gly Glu Ser Val Asp Asp Glu Leu Glu Asp Asn Ala
65                  70                  75                  80

Ile Asp Phe Leu Asn Arg Cys Gln Asp Pro Asn Gly Gly Tyr Ala Gly
                85                  90                  95

Gly Pro Gly Gln Met Pro His Ile Ala Thr Thr Tyr Ala Ala Val Asn
            100                 105                 110

Ser Leu Ile Thr Leu Gly Gly Glu Lys Ser Leu Ala Ser Ile Asn Arg
        115                 120                 125

Asp Lys Leu Tyr Gly Phe Leu Arg Arg Met Lys Gln Pro Asn Gly Gly
    130                 135                 140

Phe Arg Met His Asp Glu Gly Glu Ile Asp Val Arg Ala Cys Tyr Thr
145                 150                 155                 160

Ala Ile Ser Val Ala Ser Val Leu Asn Ile Leu Asp Asp Glu Leu Ile
                165                 170                 175

Gln Asn Val Gly Asp Tyr Ile Ile Ser Cys Gln Thr Tyr Glu Gly Gly
            180                 185                 190

Ile Ala Gly Glu Pro Gly Ser Glu Ala His Gly Gly Tyr Thr Phe Cys
        195                 200                 205

Gly Leu Ala Thr Met Ile Leu Ile Gly Glu Val Asn His Leu Asp Leu
    210                 215                 220

Pro Arg Leu Val Asp Trp Val Val Phe Arg Gln Gly Lys Glu Cys Gly
225                 230                 235                 240

Phe Gln Gly Arg Thr Asn Lys Leu Val Asp Gly Cys Tyr Ser Phe Trp
                245                 250                 255

Gln Gly Gly Ala Val Ala Leu Leu Gln Arg Leu Ser Ser Ile Ile Asn
            260                 265                 270

Lys Gln Met Glu Glu Thr Ser Gln Ile Phe Ala Val Ser Tyr Val Ser
        275                 280                 285

Glu Ala Lys Glu Ser Leu Asp Gly Thr Ser Ser His Ala Thr Cys Arg
    290                 295                 300

Gly Glu His Glu Gly Thr Ser Glu Ser Ser Ser Asp Phe Lys Asn
305                 310                 315                 320

Ile Ala Tyr Lys Phe Ile Asn Glu Trp Arg Ala Gln Glu Pro Leu Phe
                325                 330                 335

His Ser Ile Ala Leu Gln Gln Tyr Ile Leu Leu Cys Ala Gln Glu Gln
            340                 345                 350
```

Glu Gly Gly Leu Arg Asp Lys Pro Gly Lys Arg Asp His Tyr His
            355                 360                 365

Thr Cys Tyr Cys Leu Ser Gly Leu Ser Leu Cys Gln Tyr Ser Trp Ser
        370                 375                 380

Lys His Pro Asp Ser Pro Leu Pro Asn Leu Val Leu Gly Pro Tyr
385                 390                 395                 400

Ser Asn Leu Leu Glu Pro Ile His Pro Leu Phe Asn Val Val Leu Gly
                405                 410                 415

Arg Tyr Arg Glu Ala His Glu Phe Phe Phe Thr Glu Ser
            420                 425

<210> SEQ ID NO 17
<211> LENGTH: 533
<212> TYPE: DNA
<213> ORGANISM: Glycine max
<220> FEATURE:
<221> NAME/KEY: unsure
<222> LOCATION: (499)
<223> OTHER INFORMATION: n = A, C, G or T
<220> FEATURE:
<221> NAME/KEY: unsure
<222> LOCATION: (525)
<223> OTHER INFORMATION: n = A, C, G or T

<400> SEQUENCE: 17
gagagagata cgaatccggc ggcggcgcca ccgtgtccga cggtgagtca acgggaccag     60
tggatggtag agtcgcaggt gtttcagatt taccaactct tgccaccat tcctggcagc    120
gcccaaaacc tcatgttaga gctgcaacgc gataatcaca tgcagtatct ctccaaaggc    180
ctacgccatc tcagttccgc gttttctgtc ttggacgcta atcgaccctg gctctgttac    240
tggatcttcc attccattgc tttgctggga gaatccgtcg acgacgaact cgaagataac    300
actatcgatt tcttaaccg ttgccaggat ccgaatggtg atatgctggg ggaccaggc    360
cagatgcctc acattgccac aacatatgct gcagttaata cacttattac tttgggtggt    420
cagaaatcct ggcatcaatt aataggtgag ataaactgta tgggtttctg cggcggatga    480
agcaatcaaa tgggggant caagatgcat gatgaaagga gaaanttgat gtc           533

<210> SEQ ID NO 18
<211> LENGTH: 141
<212> TYPE: PRT
<213> ORGANISM: Glycine max

<400> SEQUENCE: 18

Asp Thr Asn Pro Ala Ala Pro Pro Cys Pro Thr Val Ser Gln Arg
1               5                   10                  15

Asp Gln Trp Met Val Glu Ser Gln Val Phe Gln Ile Tyr Gln Leu Phe
            20                  25                  30

Ala Thr Ile Pro Gly Ser Ala Gln Asn Leu Met Leu Glu Leu Gln Arg
        35                  40                  45

Asp Asn His Met Gln Tyr Leu Ser Lys Gly Leu Arg His Leu Ser Ser
    50                  55                  60

Ala Phe Ser Val Leu Asp Ala Asn Arg Pro Trp Leu Cys Tyr Trp Ile
65                  70                  75                  80

Phe His Ser Ile Ala Leu Leu Gly Glu Ser Val Asp Asp Glu Leu Glu
                85                  90                  95

Asp Asn Thr Ile Asp Phe Leu Asn Arg Cys Gln Asp Pro Asn Gly Gly
            100                 105                 110

```
Tyr Ala Gly Gly Pro Gly Gln Met Pro His Ile Ala Thr Thr Tyr Ala
            115                 120                 125

Ala Val Asn Thr Leu Ile Thr Leu Gly Gly Gln Lys Ser
    130                 135                 140

<210> SEQ ID NO 19
<211> LENGTH: 333
<212> TYPE: PRT
<213> ORGANISM: Pisum sativum

<400> SEQUENCE: 19

Met Ala Gly Asn Ile Glu Val Glu Glu Asp Asp Arg Val Pro Leu Arg
  1               5                  10                  15

Leu Arg Pro Glu Trp Ser Asp Val Thr Pro Ile Pro Gln Asp Asp Gly
             20                  25                  30

Pro Ser Pro Val Val Pro Ile Asn Tyr Ser Glu Glu Phe Ser Glu Val
         35                  40                  45

Met Asp Tyr Phe Arg Ala Val Tyr Phe Ala Lys Glu Leu Ser Ser Arg
 50                  55                  60

Ala Leu Ala Leu Thr Ala Glu Ala Ile Gly Leu Asn Ala Gly Asn Tyr
 65                  70                  75                  80

Thr Val Trp His Phe Arg Arg Leu Leu Leu Glu Ser Leu Lys Val Asp
                 85                  90                  95

Leu His Val Glu Arg Glu Phe Val Glu Arg Val Ala Ser Gly Asn Ser
            100                 105                 110

Lys Asn Tyr Gln Ile Trp His His Arg Arg Trp Val Ala Glu Lys Leu
        115                 120                 125

Gly Pro Glu Ala Arg Asn Ser Glu Leu Glu Phe Thr Lys Lys Ile Leu
    130                 135                 140

Ser Val Asp Ala Lys His Tyr His Ala Trp Ser His Arg Gln Trp Val
145                 150                 155                 160

Leu Gln Asn Leu Gly Gly Trp Glu Asp Glu Leu Ser Tyr Cys Ser Glu
                165                 170                 175

Leu Leu Ala Glu Asp Ile Phe Asn Asn Ser Ala Trp Asn Gln Arg Tyr
            180                 185                 190

Phe Val Ile Thr Arg Ser Pro Val Leu Gly Gly Leu Lys Ala Met Arg
        195                 200                 205

Glu Ser Glu Val Leu Phe Thr Val Glu Ala Ile Ile Ser Tyr Pro Glu
    210                 215                 220

Asn Glu Ser Ser Trp Arg Tyr Leu Arg Gly Leu Phe Lys Asp Glu Ser
225                 230                 235                 240

Thr Leu Tyr Val Asn Asp Ala Gln Val Ser Ser Leu Cys Leu Lys Ile
                245                 250                 255

Leu Lys Thr Lys Ser Asn Tyr Leu Phe Ala Leu Ser Thr Leu Leu Asp
            260                 265                 270

Leu Ser Ala Ser Val Ile Gln Pro Asn Glu Asp Phe Arg Asp Ala Ile
        275                 280                 285

Glu Ala Leu Arg Leu Gln Ile Leu Ile Lys Gln Asp Ser Asp Ile Ala
    290                 295                 300

Ile Thr Ile Cys Ser Ile Leu Glu Gln Val Asp Pro Ile Arg Val Asn
305                 310                 315                 320

Tyr Trp Val Trp Arg Lys Ser Arg Leu Pro Gln Ala Ala
                325                 330

<210> SEQ ID NO 20
```

```
<211> LENGTH: 326
<212> TYPE: PRT
<213> ORGANISM: Arabidopsis thaliana

<400> SEQUENCE: 20

Met Asn Phe Asp Glu Thr Val Pro Leu Ser Gln Arg Leu Glu Trp Ser
 1               5                  10                  15

Asp Val Val Pro Leu Thr Gln Asp Asp Gly Pro Asn Pro Val Val Pro
            20                  25                  30

Ile Ala Tyr Lys Glu Glu Phe Arg Glu Thr Met Asp Tyr Phe Arg Ala
        35                  40                  45

Ile Tyr Phe Ser Asp Glu Arg Ser Pro Arg Ala Leu Arg Leu Thr Glu
    50                  55                  60

Glu Thr Leu Leu Leu Asn Ser Gly Asn Tyr Thr Val Trp His Phe Arg
65                  70                  75                  80

Arg Leu Val Leu Glu Ala Leu Asn His Asp Leu Phe Glu Glu Leu Glu
                85                  90                  95

Phe Ile Glu Arg Ile Ala Glu Asp Asn Ser Lys Asn Tyr Gln Leu Trp
            100                 105                 110

His His Arg Arg Trp Val Ala Glu Lys Leu Gly Pro Asp Val Ala Gly
        115                 120                 125

Arg Glu Leu Glu Phe Thr Arg Arg Val Leu Ser Leu Asp Ala Lys His
    130                 135                 140

Tyr His Ala Trp Ser His Arg Gln Trp Thr Leu Arg Ala Leu Gly Gly
145                 150                 155                 160

Trp Glu Asp Glu Leu Asp Tyr Cys His Glu Leu Leu Glu Ala Asp Val
                165                 170                 175

Phe Asn Asn Ser Ala Trp Asn Gln Arg Tyr Tyr Val Ile Thr Gln Ser
            180                 185                 190

Pro Leu Leu Gly Gly Leu Glu Ala Met Arg Glu Ser Glu Val Ser Tyr
        195                 200                 205

Thr Ile Lys Ala Ile Leu Thr Asn Pro Ala Asn Glu Ser Ser Trp Arg
    210                 215                 220

Tyr Leu Lys Ala Leu Tyr Lys Asp Asp Lys Glu Ser Trp Ile Ser Asp
225                 230                 235                 240

Pro Ser Val Ser Ser Val Cys Leu Asn Val Leu Ser Arg Thr Asp Cys
                245                 250                 255

Phe His Gly Phe Ala Leu Ser Thr Leu Leu Asp Leu Leu Cys Asp Gly
            260                 265                 270

Leu Arg Pro Thr Asn Glu His Lys Asp Ser Val Arg Ala Leu Ala Asn
        275                 280                 285

Glu Glu Pro Glu Thr Asn Leu Ala Asn Leu Val Cys Thr Ile Leu Gly
    290                 295                 300

Arg Val Asp Pro Ile Arg Ala Asn Tyr Trp Ala Trp Arg Lys Ser Lys
305                 310                 315                 320

Ile Thr Val Ala Ala Ile
                325

<210> SEQ ID NO 21
<211> LENGTH: 470
<212> TYPE: PRT
<213> ORGANISM: Lycopersicon esculentum

<400> SEQUENCE: 21

Met Glu Ser Arg Lys Val Thr Lys Thr Leu Glu Asp Gln Trp Val Val
 1               5                  10                  15
```

-continued

```
Glu Arg Arg Val Arg Glu Ile Tyr Asp Tyr Phe Tyr Ser Ile Ser Pro
             20                  25                  30

Asn Ser Pro Ser Asp Leu Ile Glu Ile Glu Arg Asp Lys His Phe Gly
             35                  40                  45

Tyr Leu Ser Gln Gly Leu Arg Lys Leu Gly Pro Ser Phe Ser Val Leu
             50                  55                  60

Asp Ala Ser Arg Pro Trp Leu Cys Tyr Trp Thr Leu His Ser Ile Ala
 65                  70                  75                  80

Leu Leu Gly Glu Ser Ile Gly Gly Lys Leu Glu Asn Asp Ala Ile Asp
                 85                  90                  95

Phe Leu Thr Arg Cys Gln Asp Lys Asp Gly Tyr Gly Gly Gly Pro
            100                 105                 110

Gly Gln Met Pro His Leu Ala Thr Thr Tyr Ala Ala Val Asn Ser Leu
            115                 120                 125

Ile Thr Leu Gly Lys Pro Glu Ala Leu Ser Ser Ile Asn Arg Glu Lys
            130                 135                 140

Leu Tyr Thr Phe Leu Leu Arg Met Lys Asp Ala Ser Gly Gly Phe Arg
145                 150                 155                 160

Met His Asp Gly Gly Glu Val Asp Val Arg Ala Cys Tyr Thr Ala Ile
                165                 170                 175

Ser Val Ala Asn Ile Leu Asn Ile Val Asp Asp Glu Leu Ile His Gly
            180                 185                 190

Val Gly Asn Tyr Ile Leu Ser Cys Gln Thr Tyr Glu Gly Gly Ile Ala
            195                 200                 205

Gly Glu Pro Gly Ser Glu Ala His Gly Gly Tyr Thr Phe Cys Gly Leu
        210                 215                 220

Ala Ala Met Ile Leu Ile Asn Glu Val Asp Arg Leu Asp Leu Pro Gly
225                 230                 235                 240

Leu Ile Asp Trp Val Val Phe Arg Gln Gly Val Glu Gly Gly Phe Gln
                245                 250                 255

Gly Arg Thr Asn Lys Leu Val Asp Gly Cys Tyr Ser Phe Trp Gln Gly
            260                 265                 270

Ala Val Val Phe Leu Ile Gln Arg Leu Asn Leu Ile Val His Glu Gln
            275                 280                 285

Leu Gly Leu Ser Asn Asp Leu Ser Thr Glu Ser Ala Asp Ser Ser
        290                 295                 300

Glu Ser Glu Leu Ser Asp Glu Glu His Leu Glu Gly Ile Ser Ser
305                 310                 315                 320

His Val Gln Asp Thr Phe Pro Leu Gly Gln Ala Gly Ala Cys Gln Glu
                325                 330                 335

Asn Ala Ser His Ser Pro Lys Ile Ala Asp Thr Gly Tyr Glu Phe Ile
            340                 345                 350

Asn Arg Pro Ile Ala Met Arg Pro Leu Phe Asp Ser Met Tyr Leu Gln
            355                 360                 365

Gln Tyr Val Leu Leu Cys Ser Gln Ile Glu Val Gly Gly Phe Arg Asp
        370                 375                 380

Lys Pro Gly Lys Gly Arg Asp Tyr Tyr His Thr Cys Tyr Cys Leu Ser
385                 390                 395                 400

Gly Leu Ser Ile Ala Gln Tyr Ser Trp Thr Asp Glu Ala Asp Ser Thr
                405                 410                 415

Pro Leu Pro Arg Asp Val Phe Gly Pro Tyr Ser Lys Cys Leu Leu Glu
            420                 425                 430
```

```
Gln Val His Pro Leu Phe Asn Val Val Leu Asp Arg Tyr Tyr Glu Ala
        435                 440                 445

Arg Glu Tyr Ser Gln Ala Cys Glu Thr Val Ser Pro Leu Ser Leu Ala
450                 455                 460

Pro Thr Phe Ser Glu Thr
465                 470

<210> SEQ ID NO 22
<211> LENGTH: 419
<212> TYPE: PRT
<213> ORGANISM: Pisum sativum

<400> SEQUENCE: 22

Met Glu Ala Ser Thr Ala Ala Glu Thr Pro Thr Pro Thr Val Ser Gln
1               5                   10                  15

Arg Asp Gln Trp Ile Val Glu Ser Gln Val Phe His Ile Tyr Gln Leu
            20                  25                  30

Phe Ala Asn Ile Pro Pro Asn Ala Gln Ser Ile Ile Arg Pro Trp Leu
        35                  40                  45

Cys Tyr Trp Ile Ile His Ser Ile Ala Leu Leu Gly Glu Ser Ile Asp
    50                  55                  60

Asp Asp Leu Glu Asp Asn Thr Val Asp Phe Leu Asn Arg Cys Gln Asp
65                  70                  75                  80

Pro Asn Gly Gly Tyr Ala Gly Gly Pro Gly Gln Met Pro His Leu Ala
                85                  90                  95

Thr Thr Tyr Ala Ala Val Asn Thr Leu Ile Thr Leu Gly Gly Glu Lys
            100                 105                 110

Ser Leu Ala Ser Ile Asn Arg Asn Lys Leu Tyr Gly Phe Met Arg Arg
        115                 120                 125

Met Lys Gln Pro Asn Gly Gly Phe Arg Met His Asp Glu Gly Glu Ile
130                 135                 140

Asp Val Arg Ala Cys Tyr Thr Ala Ile Ser Val Ala Ser Val Leu Asn
145                 150                 155                 160

Ile Leu Asp Asp Glu Leu Ile Lys Asn Val Gly Asp Phe Ile Leu Ser
                165                 170                 175

Cys Gln Thr Tyr Glu Gly Gly Leu Ala Gly Glu Pro Gly Ser Glu Ala
            180                 185                 190

His Gly Gly Tyr Thr Phe Cys Gly Leu Ala Ala Met Ile Leu Ile Gly
        195                 200                 205

Glu Val Asn Arg Leu Asp Leu Pro Arg Leu Leu Asp Trp Val Val Phe
210                 215                 220

Arg Gln Gly Lys Glu Cys Gly Phe Gln Gly Arg Thr Asn Lys Leu Val
225                 230                 235                 240

Asp Gly Cys Tyr Ser Phe Trp Gln Gly Gly Ala Val Ala Leu Leu Gln
                245                 250                 255

Arg Leu His Ser Ile Ile Asp Glu Gln Met Ala Glu Ala Ser Gln Phe
            260                 265                 270

Val Thr Val Ser Asp Ala Pro Glu Glu Lys Glu Cys Leu Asp Gly Thr
        275                 280                 285

Ser Ser His Ala Thr Ser His Ile Arg His Glu Gly Met Asn Glu Ser
290                 295                 300

Cys Ser Ser Asp Val Lys Asn Ile Gly Tyr Asn Phe Ile Ser Glu Trp
305                 310                 315                 320

Arg Gln Ser Glu Pro Leu Phe His Ser Ile Ala Leu Gln Gln Tyr Ile
                325                 330                 335
```

```
Leu Leu Cys Ser Gln Glu Gln Asp Gly Gly Leu Arg Asp Lys Pro Gly
                340                 345                 350
Lys Arg Arg Asp His Tyr His Ser Cys Tyr Cys Leu Ser Gly Leu Ser
            355                 360                 365
Leu Cys Gln Tyr Ser Trp Ser Lys Arg Pro Asp Ser Pro Pro Leu Pro
        370                 375                 380
Lys Val Val Met Gly Pro Tyr Ser Asn Leu Leu Glu Pro Ile His Pro
385                 390                 395                 400
Leu Phe Asn Val Val Leu Asp Arg Tyr Arg Glu Ala His Glu Phe Phe
                405                 410                 415
Ser Gln Leu

<210> SEQ ID NO 23
<211> LENGTH: 419
<212> TYPE: PRT
<213> ORGANISM: Pisum sativum

<400> SEQUENCE: 23

Met Glu Ala Ser Thr Ala Ala Glu Thr Pro Thr Pro Thr Val Ser Gln
 1               5                  10                  15
Arg Asp Gln Trp Ile Val Glu Ser Gln Val Phe His Ile Tyr Gln Leu
                20                  25                  30
Phe Ala Asn Ile Pro Pro Asn Ala Gln Ser Ile Ile Arg Pro Trp Leu
            35                  40                  45
Cys Tyr Trp Ile Ile His Ser Ile Ala Leu Leu Gly Glu Ser Ile Asp
        50                  55                  60
Asp Asp Leu Glu Asp Asn Thr Val Asp Phe Leu Asn Arg Cys Gln Asp
65                  70                  75                  80
Pro Asn Gly Gly Tyr Ala Gly Gly Pro Gly Gln Met Pro His Leu Ala
                85                  90                  95
Thr Thr Tyr Ala Ala Val Asn Thr Leu Ile Thr Leu Gly Gly Glu Lys
                100                 105                 110
Ser Leu Ala Ser Ile Asn Arg Asn Lys Leu Tyr Gly Phe Met Arg Arg
            115                 120                 125
Met Lys Gln Pro Asn Gly Gly Phe Arg Met His Asp Glu Gly Glu Ile
        130                 135                 140
Asp Val Arg Ala Cys Tyr Thr Ala Ile Ser Val Ala Ser Val Leu Asn
145                 150                 155                 160
Ile Leu Asp Asp Glu Leu Ile Lys Asn Val Gly Asp Phe Ile Leu Ser
                165                 170                 175
Cys Gln Thr Tyr Glu Gly Gly Leu Ala Gly Glu Pro Gly Ser Glu Ala
            180                 185                 190
His Gly Gly Tyr Thr Phe Cys Gly Leu Ala Ala Met Ile Leu Ile Gly
        195                 200                 205
Glu Val Asn Arg Leu Asp Leu Pro Arg Leu Leu Asp Trp Val Val Phe
    210                 215                 220
Arg Gln Gly Lys Glu Cys Gly Phe Gln Gly Arg Thr Asn Lys Leu Val
225                 230                 235                 240
Asp Gly Cys Tyr Ser Phe Trp Gln Gly Ala Val Ala Leu Leu Gln
                245                 250                 255
Arg Leu His Ser Ile Ile Asp Glu Gln Met Ala Glu Ala Ser Gln Phe
            260                 265                 270
Val Thr Val Ser Asp Ala Pro Glu Glu Lys Glu Cys Leu Asp Gly Thr
        275                 280                 285
```

```
Ser Ser His Ala Thr Ser His Ile Arg His Glu Gly Met Asn Glu Ser
    290             295             300

Cys Ser Ser Asp Val Lys Asn Ile Gly Tyr Asn Phe Ile Ser Glu Trp
305             310             315             320

Arg Gln Ser Glu Pro Leu Phe His Ser Ile Ala Leu Gln Gln Tyr Ile
                325             330             335

Leu Leu Cys Ser Gln Glu Gln Asp Gly Gly Leu Arg Asp Lys Pro Gly
            340             345             350

Lys Arg Arg Asp His Tyr His Ser Cys Tyr Cys Leu Ser Gly Leu Ser
            355             360             365

Leu Cys Gln Tyr Ser Trp Ser Lys Arg Pro Asp Ser Pro Pro Leu Pro
    370             375             380

Lys Val Val Met Gly Pro Tyr Ser Asn Leu Leu Glu Pro Ile His Pro
385             390             395             400

Leu Phe Asn Val Val Leu Asp Arg Tyr Arg Glu Ala His Glu Phe Phe
            405             410             415

Ser Gln Leu
```